(12) United States Patent
Blaschke et al.

(10) Patent No.: US 6,648,133 B1
(45) Date of Patent: Nov. 18, 2003

(54) DEVICE AND METHOD FOR HYDRATING AND REHYDRATING ORTHOPEDIC GRAFT MATERIALS

(75) Inventors: R. Craig Blaschke, Warsaw, IN (US); Daniel B. Smith, Warsaw, IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/908,151

(22) Filed: Jul. 18, 2001

(51) Int. Cl.[7] ............................................... B65D 25/08
(52) U.S. Cl. ..................... 206/221; 206/438; 206/524.8
(58) Field of Search ................................. 206/221, 219, 206/438, 524.1, 524.8; 604/410, 416

(56) References Cited

U.S. PATENT DOCUMENTS

| | | |
|---|---|---|
| 3,074,544 A | 1/1963 | Bollmeier et al. |
| 3,294,227 A | 12/1966 | Schneider et al. |
| 3,608,709 A | 9/1971 | Pike |
| 4,463,875 A | 8/1984 | Tepic |
| 4,467,588 A | 8/1984 | Carveth |
| 5,370,221 A | 12/1994 | Magnusson et al. |
| 5,398,483 A | 3/1995 | Smith et al. |
| 5,501,520 A | 3/1996 | Lidgren et al. |
| 5,588,745 A | 12/1996 | Tanaka et al. |
| 5,934,803 A | 8/1999 | Hutter |
| 6,083,229 A * | 7/2000 | Constantz et al. .......... 206/219 |
| 6,149,655 A | 11/2000 | Constantz et al. |
| 6,286,670 B1 * | 9/2001 | Smith ......................... 206/221 |

* cited by examiner

Primary Examiner—Luan K. Bui
(74) Attorney, Agent, or Firm—Harness, Dickey & Pierce, P.L.C.

(57) ABSTRACT

A vacuum package system for hydrating and/or rehydrating orthopedic graft materials, such as allograft materials, xenograft materials, and synthetic materials, is described. The system primarily includes a container, which includes a dividing device for dividing the container into first and second compartments and for isolating the compartments from one another, the first compartment containing a liquid component and the second compartment containing either dry porous and/or dehydrated orthopedic graft material under vacuum. An elongated pocket portion extends from, and is in communication with, the second compartment. A vacuum reservoir device is disposed within the pocket portion and is in communication with the second compartment. The vacuum reservoir device is capable of taking up substantially all residual interstitial gases and thereby ensuring thorough infusion of the liquid component into the orthopedic graft material component upon release of the dividing device so as to form either a hydrated and/or rehydrated orthopedic graft material. An optional gas permeable membrane is disposed between the second compartment and the pocket portion.

65 Claims, 6 Drawing Sheets

DEVICE AND METHOD FOR HYDRATING AND REHYDRATING ORTHOPEDIC GRAFT MATERIALS

FIELD OF THE INVENTION

The present invention relates generally to orthopedic materials and packaging therefor, and more particularly to a device and method for hydrating and/or rehydrating orthopedic graft materials, such as allograft materials, xenograft materials, and synthetic materials. Specifically, a vacuum package system is provided for dehydrated, e.g., freeze-dried, orthopedic graft materials, as well as dry porous orthopedic graft materials, e.g., calcium-phosphate-based materials, which allows for liquid materials to rapidly and thoroughly infuse within the pores of either type of orthopedic graft material so as to form hydrated and/or rehydrated orthopedic graft materials.

BACKGROUND OF THE INVENTION

Allografting is one of the most widely used orthopedic transplantation techniques currently being used by orthopedic surgeons. Its main use is in the field of revision joint replacement, particularly total hip replacement, although its use is also widespread in the treatment of many different types of bone defects as well.

An allograft is generally defined as a graft of tissue, such as bone tissue, from a donor of one species and grafted into a recipient of the same species. Allograft tissue is typically derived from cadaveric donors (i.e., from deceased donors).

One type of allograft tissue is generally referred to as structural allograft tissue, which typically consist of blocks of bone or other types of tissue that can fastened to one or more surfaces of the bone defect. These blocks can also act as bulk supports to orthopedic prostheses or other types of graft tissue. These blocks can be shaped into any number of appropriate shapes and configurations in order to suit the particular clinical needs of the patient.

In order to preserve the useful shelf life of allograft tissue, as well as to inhibit bacterial growth within the allograft tissue, it is becoming common practice to dehydrate the allograft tissue, especially by freeze-drying. Freeze-drying quickly removes virtually all of the moisture within the allograft tissue, thus inhibiting any subsequent bacterial growth. However, prior to employing the allograft tissue in a surgical setting, it is generally necessary to re-hydrate the freeze-dried allograft tissue with some sort of fluid, such as sterilized water, saline, or the like.

Typically, the freeze-dried allograft tissue is removed from its protective packaging and either introduced into a liquid source or the liquid source is introduced onto the freeze-dried allograft tissue. This is a cumbersome and sometimes sloppy process that unnecessarily exposes the freeze-dried allograft tissue to atmospheric pathogens during the rehydration process. Additionally, this haphazard process does not ensure that the liquid material will thoroughly infuse into the pores of the allograft tissue.

Additionally, xenograft materials (e.g., non-human or animal-based graft materials) as well as synthetic materials (e.g., ceramic graft materials such as calcium-based materials, calcium-phosphate-based materials, calcium-sulfate-based materials, calcium-sodium-phosphate-based materials, as well as many others) have been used as orthopedic graft materials as well. However, these materials, must also be either rehydrated, in the case of dehydrated xenografts, or hydrated in the case of dry porous synthetic materials. Therefore, the same general problems described above are also encountered with these materials as well.

Therefore, there still exists a need for an apparatus and method for either hydrating dry porous orthopedic graft materials or rehydrating dehydrated orthopedic graft materials such that the respective orthopedic graft materials can be either hydrated and/or rehydrated in a sterile, efficient, and cost-effective manner.

SUMMARY OF THE INVENTION

In accordance with one embodiment of the present invention, a container for storing orthopedic graft materials is provided, comprising: (1) a dividing device for dividing the container into first and second compartments and for isolating the compartments from one another, the first compartment capable of receiving a liquid component and the second compartment containing an orthopedic graft material under vacuum; and (2) a vacuum reservoir device in communication with the second compartment, the vacuum reservoir device being capable of taking up substantially all residual interstitial gases and thereby ensuring thorough infusion of the liquid component into the orthopedic graft material component upon release of the dividing device so as to form a hydrated orthopedic graft material.

In accordance with a second embodiment of the present invention, a container for storing orthopedic materials is provided, comprising: (1) a dividing device for dividing the container into first and second compartments and for isolating the compartments from one another, the first compartment containing a liquid component and the second compartment containing an orthopedic graft material under vacuum; and (2) a vacuum reservoir device in communication with the second compartment, the vacuum reservoir device being capable of taking up substantially all residual interstitial gases and thereby ensuring thorough infusion of the liquid component into the orthopedic graft material component upon release of the dividing device so as to form a hydrated orthopedic graft material.

In accordance with a third embodiment of the present invention, a container for storing orthopedic graft materials is provided, comprising: (1) a dividing device for dividing the container into first and second compartments and for isolating the compartments from one another, the first compartment containing a liquid component and the second compartment containing an orthopedic graft material under vacuum; (2) an elongated pocket portion extending from and in communication with the second compartment; (3) a gas permeable membrane disposed between the second compartment and the pocket portion; and (4) a vacuum reservoir device disposed within the pocket portion and being in communication with the second compartment, the vacuum reservoir device being capable of taking up substantially all residual interstitial gases and thereby ensuring thorough infusion of the liquid component into the orthopedic graft material component upon release of the dividing device so as to form a rehydrated orthopedic graft material.

In accordance with a fourth embodiment of the present invention, a method for hydrating an orthopedic graft material is provided, comprising: (1) providing a container, including: (a) a dividing device for dividing the container into first and second compartments and for isolating the compartments from one another, the first compartment capable of receiving a liquid component and the second compartment containing an orthopedic graft material under vacuum; and (b) a vacuum reservoir device in communication with the second compartment, the vacuum reservoir device being capable of taking up substantially all residual interstitial gases and thereby ensuring thorough infusion of the liquid component into the orthopedic graft material component upon release of the dividing device so as to form a hydrated orthopedic graft material; and (2) releasing the dividing device, whereupon the liquid component rapidly migrates into the second compartment and thoroughly infuses into the orthopedic graft material component so as to form a hydrated orthopedic graft material.

In accordance with a fifth embodiment of the present invention, a method for hydrating an orthopedic graft material is provided, comprising: (1) providing a container, including: (a) a dividing device for dividing the container into first and second compartments and for isolating the compartments from one another, the first compartment containing a liquid component and the second compartment containing the orthopedic graft material under vacuum; and (b) a vacuum reservoir device in communication with the second compartment, the vacuum reservoir device being capable of taking up substantially all residual interstitial gases; and (2) releasing the dividing device, whereupon the liquid component rapidly migrates into the second compartment and thoroughly infuses into the orthopedic graft material component so as to form a hydrated orthopedic graft material.

In accordance with a sixth embodiment of the present invention, a method for hydrating an orthopedic graft material is provided, comprising: (1) providing a container, including: (a) a dividing device for dividing the container into first and second compartments and for isolating the compartments from one another, the first compartment containing a liquid component and the second compartment containing the orthopedic graft material under vacuum; (b) an elongated pocket portion extending from and in communication with the second compartment; (c) a gas permeable membrane disposed between the second compartment and the pocket portion; and (d) a vacuum reservoir device disposed within the pocket portion and being in communication with the second compartment, the vacuum reservoir device being capable of taking up substantially all residual interstitial gases; and (2) releasing the dividing device, whereupon the liquid component rapidly migrates into the second compartment and thoroughly infuses into the orthopedic graft material component so as to form a hydrated orthopedic graft material.

A more complete appreciation of the present invention and its scope can be obtained from the following detailed description of the invention, the drawings, and the appended claims.

BRIEF DESCRIPTION OF THE DRAWINGS

The present invention will become more fully understood from the detailed description and the accompanying drawings, wherein.

The same reference numerals refer to the same parts throughout the various Figures.

DETAILED DESCRIPTION OF THE INVENTION

The present invention is useful for the hydration and rehydration of any number of different orthopedic graft materials, such as but not limited to allograft materials (e.g., human-based graft materials), xenograft materials (e.g., non-human or animal-based graft materials), and synthetic materials (e.g., ceramic graft materials such as calcium-based materials, calcium-phosphate-based materials, calcium-sulfate-based materials, calciumsodium-phosphate-based materials, as well as many others).

These various orthopedic graft materials, especially the synthetic materials, can be shaped into any number of configurations, including but not limited to blocks, rings, struts, machined shapes, chips, morsels, granules, and so forth.

Furthermore, ceramic cements, such as but not limited to tetracalcium phosphate/tricalcium phosphate cement, calcium sodium phosphate cement, and calcium sulfate, may also be used as orthopedic graft materials. The powder portion would typically be mixed with a citric acid solution or a citrate salt solution in order to form a thick paste which hardens in 5 to 15 minutes.

By the term "orthopedic graft material," as that term is used herein, it is meant any orthopedic material that is capable of either being hydrated and/or rehydrated. By the term "rehydrated," as that term is used herein, it is meant either hydrated and/or rehydrated.

The hydrating and/or rehydrating material may be comprised of any number of aqueous-based liquids, such as water, saline, or the like. Additionally, biologically active materials (e.g., therapeutic and/or prophylactic), such as but not limited to antibiotics, platelet concentrates, bone growth factors, may be introduced into the hydrating and/or rehydrating material, or alternatively, may comprise a portion of, or the entire volume of, the hydrating and/or rehydrating material.

Figure 1:
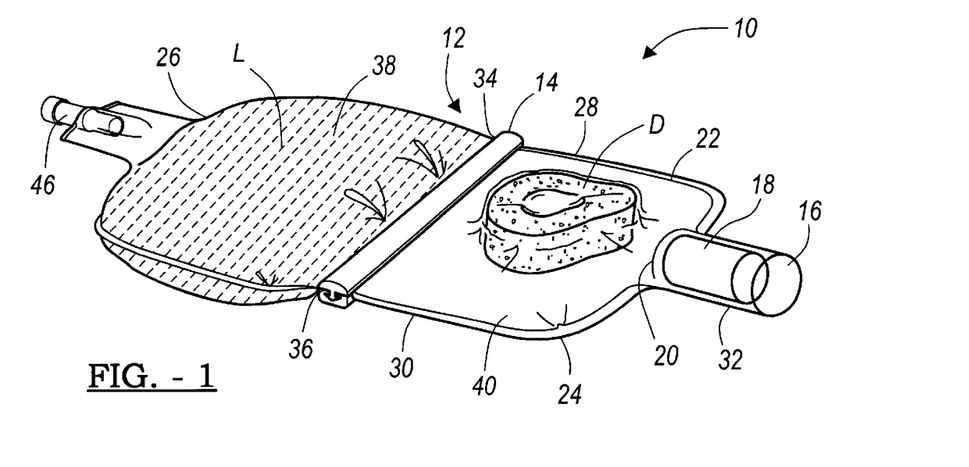
FIG. 1 illustrates a perspective view of a packaging system for orthopedic graft materials, in accordance with one embodiment of the present invention.
Figure 2:
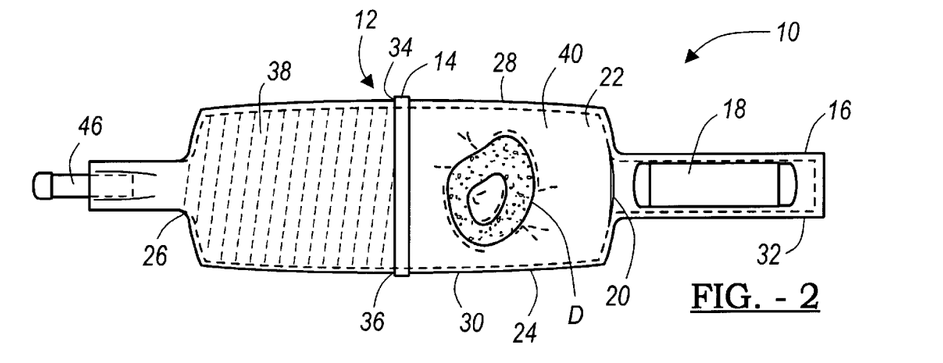
FIG. 2 illustrates a top plan view of a packaging system for orthopedic materials, in accordance with one embodiment of the present invention.
Figure 3:
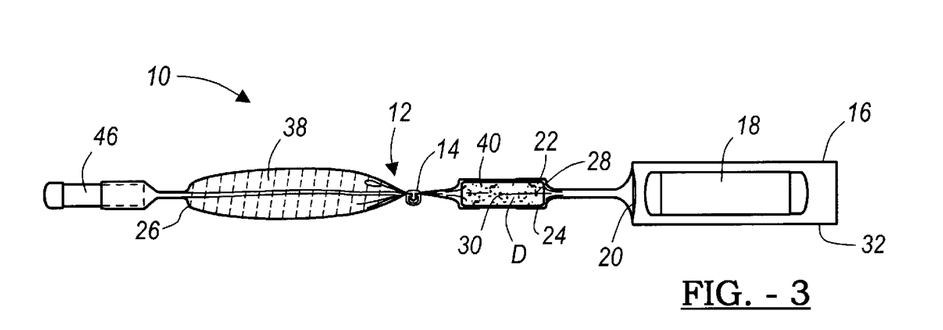
FIG. 3 illustrates a side elevational view of a packaging system for orthopedic materials, in accordance with one embodiment of the present invention.

Referring now to FIGS. 1–3, a packaging system for orthopedic materials is shown designated generally by the reference numeral 10. The packaging system 10 is somewhat similar to the packaging systems described in U.S. Pat. Nos. 5,370,221 and 5,398,483, the entire specifications of which are incorporated herein by reference.

Figure 1A:
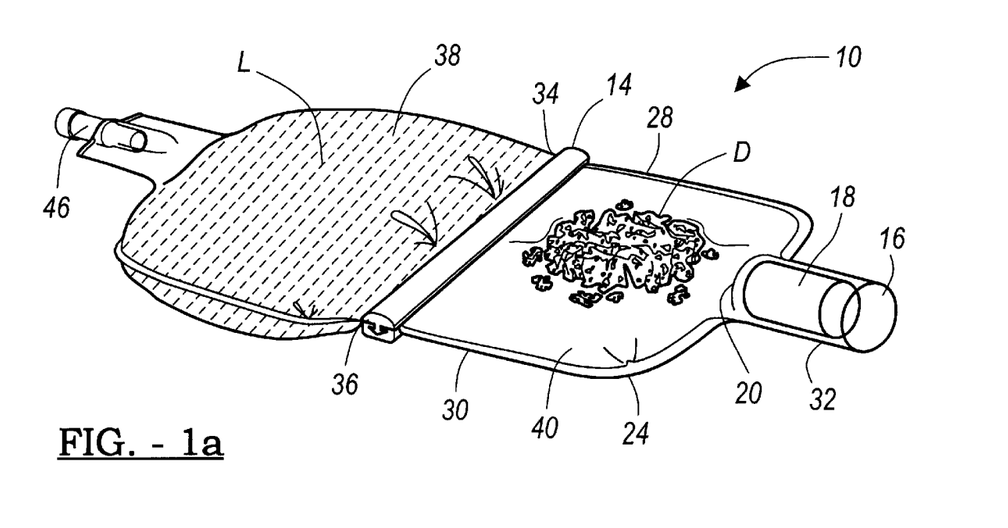
FIG. 1a illustrates a perspective view of a packaging system for morselized orthopedic graft materials, in accordance with one embodiment of the present invention.
Figure 1B:
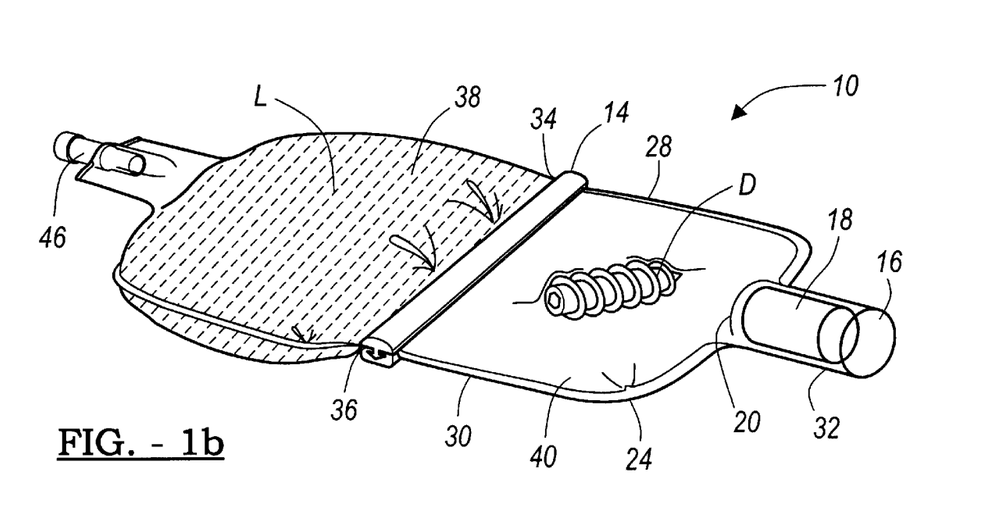
FIG. 1b illustrates a perspective view of a packaging system for machined shape synthetic orthopedic graft materials, in accordance with one embodiment of the present invention.

The packaging system 10 of the present invention primarily includes a preferably flexible container 12, a divider or clamp 14, a tubular portion 16, a vacuum reservoir 18, and an optional gas permeable membrane 20. Preferably, the optional gas permeable membrane 20 is also substantially liquid impermeable. By way of a non-limiting example, the material to be stored can be either substantially solid allograft materials (FIG. 1), morselized allograft materials (FIG. 1a), xenograft materials (not shown), synthetic materials (FIG. 1b), as well as other types of orthopedic graft materials.

The container 12 preferably includes a front panel 22 and a rear panel 24, each made of a thin generally impervious flexible film or laminate. The exact nature of the thin generally impervious flexible film or laminate to be used with the container 12 of the present invention depends upon the nature of the materials to be stored and the conditions under which the materials will be combined and used. For many applications and materials, films and/or laminates of polyethylene, TEFLON, polyester, nylon, ethyl vinyl alcohol, metal foil, laminated glass and various combinations of the foregoing materials may be used. However, it will be appreciated that other suitable materials may also be used as well.

Additionally, while the container 12 is shown as being substantially rectangular, it is to be understood that the present invention is applicable to flexible containers of other shapes, such as square, triangular or trapezoidal and may have curved edges.

The panels 22 and 24 can be formed from a single sheet of flexible film sealed to each other at a bottom edge 26 and side edges 28 and 30.

As noted, the container 12 further includes a tubular portion 16 which is sealed along its continuous edge 32 similar to the edges 26, 28, and 30. Disposed within the tubular portion 16 is the vacuum reservoir device 18, the purpose of which will be more fully explained herein.

The clamp 14 is arranged to provide a temporary seal of the inner surfaces of the panels 20 and 22 to each other along a line extending from an initial point 34 on the sealed edge 28 to a terminal point 36 on the sealed edge 30 to form a first or upper compartment 38 and a second or lower compartment 40. As will be appreciated by those skilled in the art, the clamp 14 is preferably placed on the container 12 prior to being filled with either the liquid component or the orthopedic graft material component.

Figure 4:
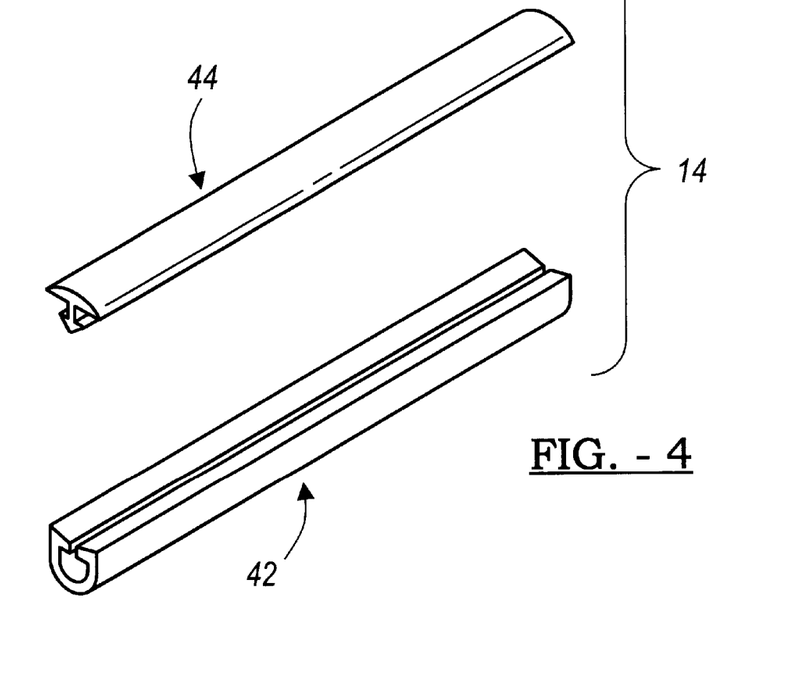
FIG. 4 illustrates an exploded view of a clamp of the packaging system for orthopedic materials, in accordance with one embodiment of the present invention.
Figure 5:
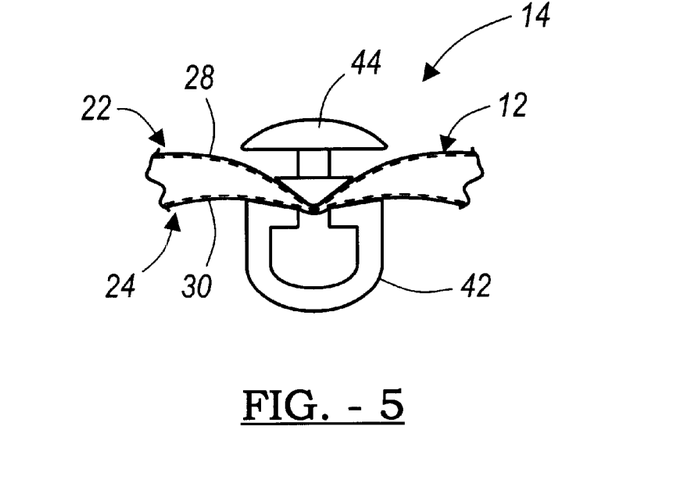
FIG. 5 illustrates a partial cross-sectional view of the clamp of the packaging system for orthopedic materials, in accordance with one embodiment of the present invention.

Referring to FIGS. 4–5, the clamp 14 comprises a C-shaped outer retention member 42 and an I-shaped inner retention member 44 which partially fits within the hollow of the C-shaped outer retention member 42. When the clamp 14 is assembled with respect to the container 12 as shown in FIG. 5, the outer retention member 42 is positioned on the outside of the rear panel 22 and the inner retention member 44 is positioned on the outside of the front panel 20 such that the panels 20 and 22 are pinched together along a pair of parallel lines extending from the initial point 34 to the terminal point 36. The inner retention member 44 has a contoured upper end which fits within the inner hollow of outer retention member 42 and has a thickness substantially equal to the inner distance between the open ends of the C-shaped section of the outside retention member 42 so that a double thickness of panels 20 and 22 is tightly compressed along a pair of parallel lines to form an effective seal or divider. The outer retention member 42 is made of a resilient material so that the inner retention member 44 may be forced into position therein by placing it over the entire length of the opening of the outer retention member 42 and then pressing it into place. Inner retention member 44 has a contoured upper end which can open the open ends of the C-shaped section of the outside retention member 42 to accommodate the inner retention member 44.

The nature of the clamp 14 may also vary. The clamp 14 described in connection with the present invention consisting of an I-shaped inner retention member 44 and a C-shaped outer retention member 42, is preferred because of its simplicity and ease of handling. However, other types of clamps suitable for applying pressure to the container 12 may also be used. In addition, it is possible to replace the clamp 14 with an additional separation seal or divider (not shown). In this embodiment, the separation seal can be either a heat seal or an adhesive seal to separate the upper compartment 38 from the lower compartment 40. The strength of this separation seal must be such that it can be broken by placing pressure on either of the compartments 38 and 40 without damaging the panels 20 and 22. This separation seal may also be used in conjunction with the clamp 14.

Figure 6:
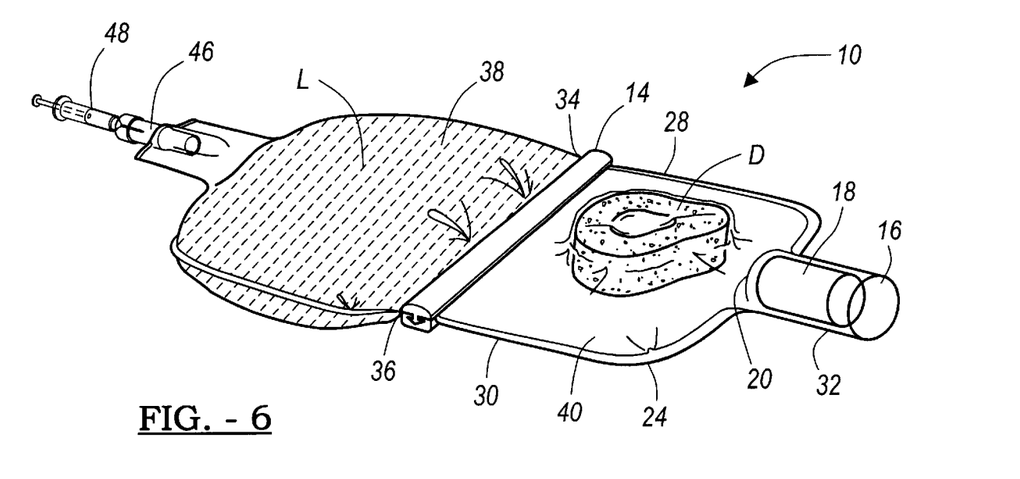
FIG. 6 illustrates a perspective view of a material introduction device on the packaging system for orthopedic materials, in accordance with one embodiment of the present invention.

The method of packaging the components of the orthopedic graft materials within the packaging 12 will now be described. The side edges 26 and 28 of the front panel 20 and the rear panel 22 are typically secured together by heat sealing, although other means of sealing may be used as well, such as adhesives. The clamp 14 is then placed over the front panel 20 and the rear panel 22 so as to form a temporary seal between the front panel 20 and the rear panel 22 and partially form the upper compartment 38 and the lower compartment 40 under environmentally controlled conditions. In certain circumstances, it will be necessary to position the orthopedic graft material D within the lower compartment 40 prior to heat sealing of the respective edges of the lower compartment 40 due, in part, to the size and configuration of the orthopedic graft material. In that circumstance, once the orthopedic graft material D is properly positioned, a heat seal then closes the lower compartment 40. The container 12 is then sterilized employing gamma radiation, electron beam or other means. The liquid component L (e.g., water, saline, or the like) is then filled into the upper compartment 38 under aseptic conditions and then the upper compartment 38 is closed by the seal 24. However, it should be noted that it is not necessary that the liquid component L be added at the same time the orthopedic graft material D is introduced. For example, the liquid component L can be introduced immediately before the infusion process is to take place, for example, in the operating room. Additionally, a port device 46 may be provided on the upper compartment 38 in order to introduce additional materials into the liquid component L (via syringe 48), such as but not limited to biologically active materials, as shown in FIG. 6. Preferably, the port device 46 is self-sealing, or is provided with a cap or similar device, so as to prevent any leakage problems.

The main benefit of the present invention is that it provides a system for in situ mixing of the two components to produce a rehydrated orthopedic graft material. This is achieved by maintaining the lower compartment 40 under vacuum. This vacuum condition is facilitated by the presence of the vacuum reservoir 18 in the tubular portion 16. The vacuum reservoir 18 preferably has a sufficiently large volume to take up the residual gases which will be replaced in the interstitial voids between the particles of the orthopedic graft material by the liquid component upon release or breaking of the seal between the first and second compartments. The purpose of the optional gas permeable membrane 20 is to allow air to be drawn out of the lower compartment 40 (e.g., during the creation of the vacuum condition), while preventing any liquid or particulate matter from penetrating into the tubular portion 16.

Figure 7:
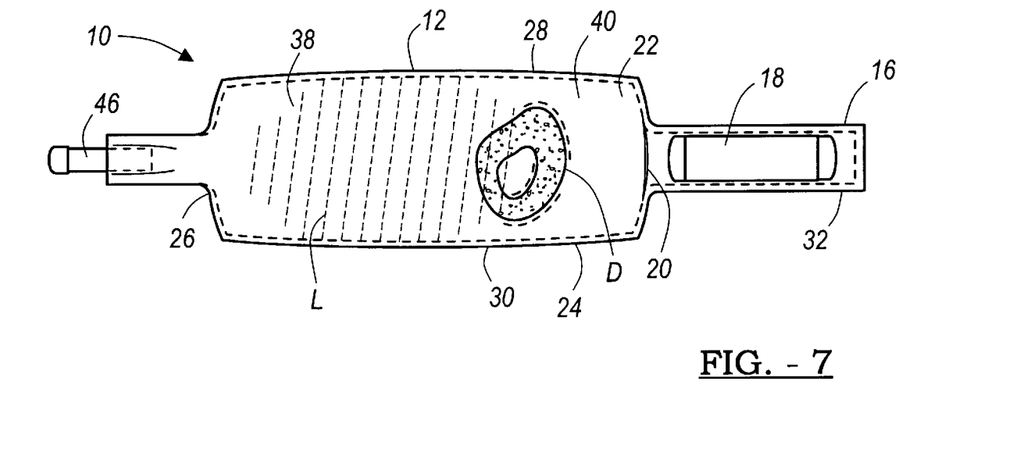
FIG. 7 illustrates a top plan view of the initial infusion process of the dehydrated orthopedic graft material, in accordance with one embodiment of the present invention.
Figure 8:
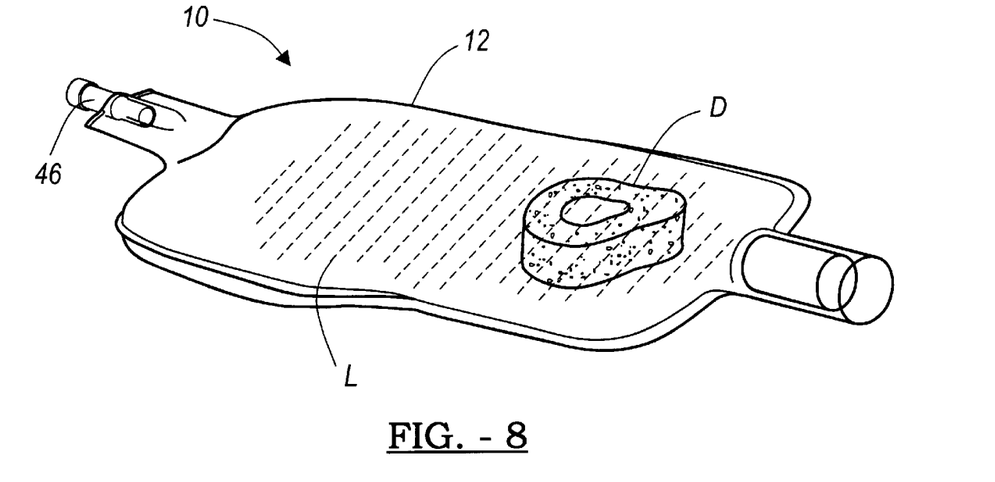
FIG. 8 illustrates a perspective view of the initial infusion process of the dehydrated orthopedic graft material, in accordance with one embodiment of the present invention.
Figure 9:
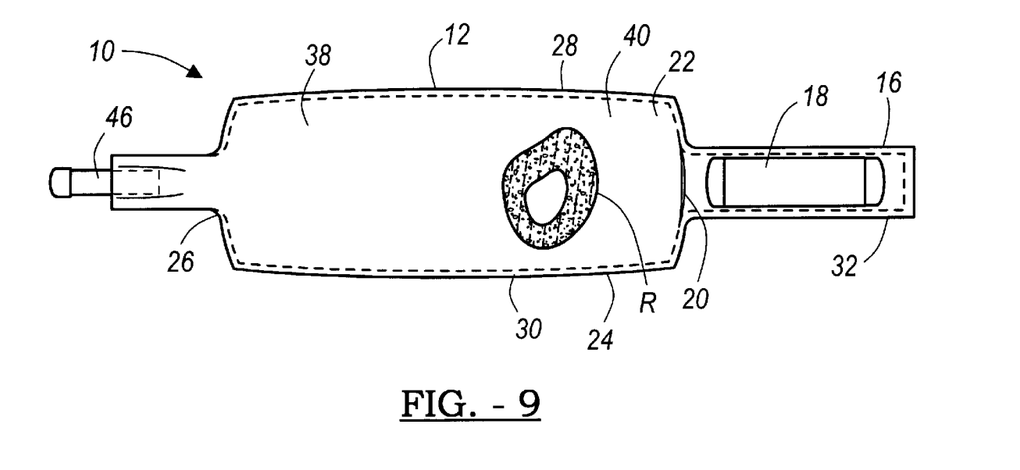
FIG. 9 illustrates a top plan view of the completion of the infusion process of the dehydrated orthopedic graft material, in accordance with one embodiment of the present invention.
Figure 10:
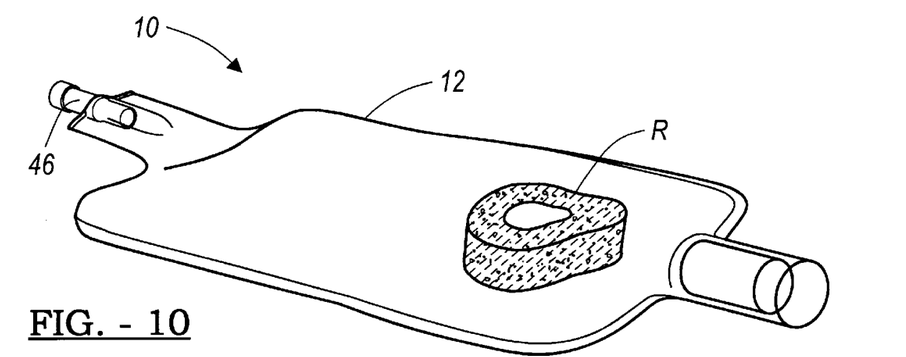
FIG. 10 illustrates a perspective view of the completion of the infusion process of the dehydrated orthopedic graft material, in accordance with one embodiment of the present invention.
Figure 11:
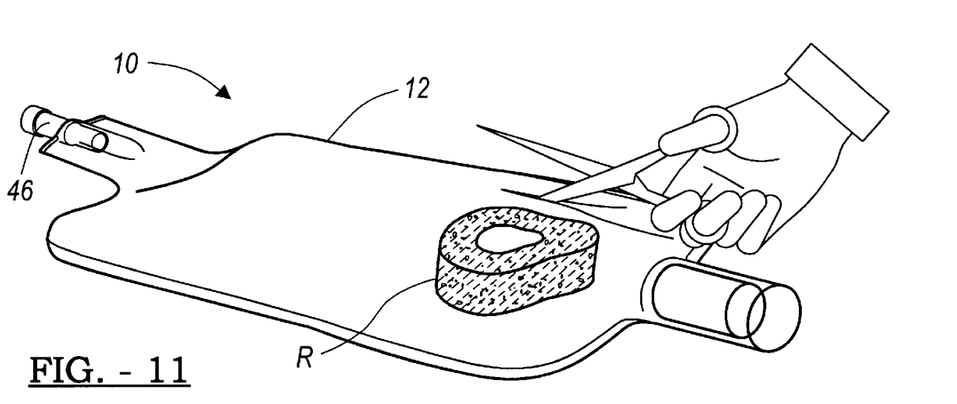
FIG. 11 illustrates a perspective view of the opening of the packaging system for orthopedic materials, in accordance with one embodiment of the present invention.
Figure 12:
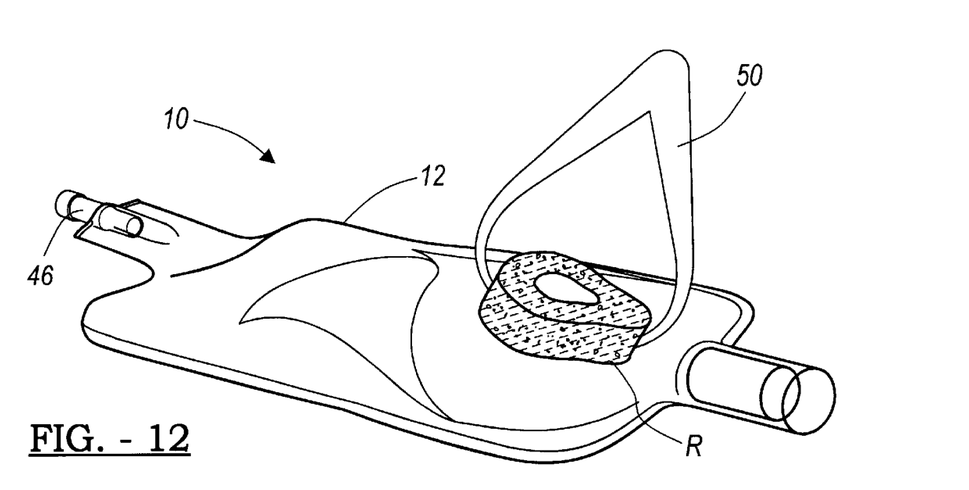
FIG. 12 illustrates a perspective view of the rehydrated orthopedic graft material being removed from the packaging system for orthopedic materials, in accordance with one embodiment of the present invention.

The force which transfers the liquid component L into the second compartment 40 to combine with the orthopedic graft material component D is thus the pressure differential between the atmospheric pressure acting on the walls of the first compartment 38 and the pressure prevailing in the second compartment 40. The function of the vacuum reservoir 18 is to maintain a sufficiently low pressure in the second compartment 40 until the orthopedic graft material component D has been completely and thoroughly infused by the liquid component L. Once the clamp 14 has been removed, the liquid component L will rapidly flow into the second compartment 40, completely and thoroughly infusing the orthopedic graft material component D, as shown in FIGS. 7–8. Once the infusion process is complete, the hydrated (or rehydrated) orthopedic graft material R will be ready for immediate implantation, as shown in FIGS. 9–10 Following the infusion process, the container 12 holding the hydrated/rehydrated orthopedic graft material R is opened (see FIG. 11) and the hydrated/rehydrated graft material R is removed (see FIG. 12), preferably with a sterile instrument such as a forceps 50, and is now ready for immediate affixation onto a bone defect, for example.

The foregoing description is considered illustrative only of the principles of the invention. Furthermore, because numerous modifications and changes will readily occur to those skilled in the art, it is not desired to limit the invention to the exact construction and process shown as described above. Accordingly, all suitable modifications and equivalents that may be resorted to that fall within the scope of the invention as defined by the claims that follow.

What is claimed is:

1. A container for storing orthopedic graft materials, comprising:
  a dividing device for dividing the container into first and second compartments and for isolating the compartments from one another, the first compartment capable of receiving a liquid component and the second compartment containing an orthopedic graft material under vacuum; and
  a vacuum reservoir device in communication with the second compartment, the vacuum reservoir device being capable of taking up substantially all residual interstitial gases and thereby ensuring thorough infusion of the liquid component into the orthopedic graft material component upon release of the dividing device so as to form a hydrated orthopedic graft material.

2. The invention according to claim 1, further comprising the liquid component being contained within the first compartment.

3. The invention according to claim 1, further comprising an elongated pocket portion extending from and in communication with the second compartment, wherein the vacuum reservoir device is disposed within the pocket portion.

4. The invention according to claim 3, further comprising a gas permeable membrane disposed between the second compartment and the pocket portion.

5. The invention according to claim 4, wherein the gas permeable membrane only permits the transmission of gaseous fluids therethrough.

6. The invention according to claim 1, wherein the dividing device includes a heat seal between the first and second compartments, the heat seal including an opening for passing the liquid component into the second compartment and a clamp in removably interlocked relationship with the heat seal to removably close the opening.

7. The invention according to claim 1, wherein the orthopedic graft material is selected from the group consisting of allograft material, xenograft material, synthetic material, and combinations thereof.

8. The invention according to claim 1, wherein the liquid component is a water-based liquid.

9. The invention according to claim 1, wherein the liquid component is a salt-containing liquid.

10. The invention according to claim 1, further comprising a biologically active material being present in the liquid component.

11. The invention according to claim 10, wherein the biologically active material is an antibiotic.

12. The invention according to claim 10, wherein the biologically active material is a platelet concentrate.

13. The invention according to claim 1, further comprising at least one material introduction device in communication with the first compartment.

14. The invention according to claim 1, wherein the orthopedic graft material component is a substantially dry and porous material.

15. The invention according to claim 1, wherein the orthopedic graft material component is a substantially dehydrated material.

16. The invention according to claim 1, wherein the orthopedic graft material component is a substantially freeze-dried material.

17. A container for storing orthopedic graft materials, comprising:
  a dividing device for dividing the container into first and second compartments and for isolating the compartments from one another, the first compartment containing a liquid component and the second compartment containing an orthopedic graft material under vacuum; and
  a vacuum reservoir device in communication with the second compartment, the vacuum reservoir device being capable of taking up substantially all residual interstitial gases and thereby ensuring thorough infusion of the liquid component into the orthopedic graft material component upon release of the dividing device so as to form a hydrated orthopedic graft material.

18. The invention according to claim 17, further comprising an elongated pocket portion extending from and in communication with the second compartment, wherein the vacuum reservoir device is disposed within the pocket portion.

19. The invention according to claim 18, further comprising a gas permeable membrane disposed between the second compartment and the pocket portion.

20. The invention according to claim 19, wherein the gas permeable membrane only permits the transmission of gaseous fluids therethrough.

21. The invention according to claim 17, wherein the dividing device includes a heat seal between the first and second compartments, the heat seal including an opening for passing the liquid component into the second compartment and a clamp in removably interlocked relationship with the heat seal to removably close the opening.

22. The invention according to claim 17, wherein the orthopedic graft material is selected from the group consisting of allograft material, xenograft material, synthetic material, and combinations thereof.

23. The invention according to claim 17, wherein the liquid component is a water-based liquid.

24. The invention according to claim 17, wherein the liquid component is a salt-containing liquid.

25. The invention according to claim 17, further comprising a biologically active material being present in the liquid component.

26. The invention according to claim 25, wherein the biologically active material is an antibiotic.

27. The invention according to claim 25, wherein the biologically active material is a platelet concentrate.

28. The invention according to claim 17, further comprising at least one material introduction device in communication with the first compartment.

29. The invention according to claim 17, wherein the orthopedic graft material component is a substantially dry and porous material.

30. The invention according to claim 17, wherein the orthopedic graft material component is a substantially dehydrated material.

31. The invention according to claim 17, wherein the orthopedic graft material component is a substantially freeze-dried material.

32. A container for storing orthopedic graft materials, comprising:
a dividing device for dividing the container into first and second compartments and for isolating the compartments from one another, the first compartment containing a liquid component and the second compartment containing an orthopedic graft material under vacuum;
an elongated pocket portion extending from and in communication with the second compartment;
a gas permeable membrane disposed between the second compartment and the pocket portion; and
a vacuum reservoir device disposed within the pocket portion and being in communication with the second compartment, the vacuum reservoir device being capable of taking up substantially all residual interstitial gases and thereby ensuring thorough infusion of the liquid component into the orthopedic graft material component upon release of the dividing device so as to form a rehydrated orthopedic graft material.

33. The invention according to claim 32, wherein the gas permeable membrane only permits the transmission of gaseous fluids therethrough.

34. The invention according to claim 32, wherein the dividing device includes a heat seal between the first and second compartments, the heat seal including an opening for passing the liquid component into the second compartment and a clamp in removably interlocked relationship with the heat seal to removably close the opening.

35. The invention according to claim 32, wherein the orthopedic graft material is selected from the group consisting of allograft material, xenograft material, synthetic material, and combinations thereof.

36. The invention according to claim 32, wherein the liquid component is a water-based liquid.

37. The invention according to claim 32, wherein the liquid component is a salt-containing liquid.

38. The invention according to claim 32, further comprising a biologically active material being present in the liquid component.

39. The invention according to claim 38, wherein the biologically active material is an antibiotic.

40. The invention according to claim 38, wherein the biologically active material is a platelet concentrate.

41. The invention according to claim 32, further comprising at least one material introduction device in communication with the first compartment.

42. The invention according to claim 32, wherein the orthopedic graft material component is a substantially dry and porous material.

43. The invention according to claim 32, wherein the orthopedic graft material component is a substantially dehydrated material.

44. The invention according to claim 32, wherein the orthopedic graft material component is a substantially freeze-dried material.

45. A method for hydrating an orthopedic graft material, comprising:
providing a container, including:
a dividing device for dividing the container into first and second compartments and for isolating the compartments from one another, the first compartment capable of receiving a liquid component and the second compartment containing an orthopedic graft material under vacuum; and
a vacuum reservoir device in communication with the second compartment, the vacuum reservoir device being capable of taking up substantially all residual interstitial gases and thereby ensuring thorough infusion of the liquid component into the orthopedic graft material component upon release of the dividing device so as to form a hydrated orthopedic graft material; and
releasing the dividing device, whereupon the liquid component rapidly migrates into the second compartment and thoroughly infuses into the orthopedic graft material component so as to form a hydrated orthopedic graft material.

46. The invention according to claim 45, further comprising removing the hydrated orthopedic graft material from the container.

47. The invention according to claim 46, further comprising fastening the hydrated orthopedic graft material onto the surface of bone tissue.

48. A method for hydrating an orthopedic graft material, comprising:
providing a container, including:
a dividing device for dividing the container into first and second compartments and for isolating the compartments from one another, the first compartment containing a liquid component and the second compartment containing the orthopedic graft material under vacuum; and
a vacuum reservoir device in communication with the second compartment, the vacuum reservoir device being capable of taking up substantially all residual interstitial gases; and
releasing the dividing device, whereupon the liquid component rapidly migrates into the second compartment and thoroughly infuses into the orthopedic graft material component so as to form a hydrated orthopedic graft material.

49. The invention according to claim 48, further comprising removing the hydrated orthopedic graft material from the container.

50. The invention according to claim 49, further comprising fastening the hydrated orthopedic graft material onto the surface of bone tissue.

51. A method for hydrating an orthopedic graft material, comprising:

providing a container, including:
- a dividing device for dividing the container into first and second compartments and for isolating the compartments from one another, the first compartment containing a liquid component and the second compartment containing the orthopedic graft material under vacuum;
- an elongated pocket portion extending from and in communication with the second compartment;
- a gas permeable membrane disposed between the second compartment and the pocket portion; and
- a vacuum reservoir device disposed within the pocket portion and being in communication with the second compartment, the vacuum reservoir device being capable of taking up substantially all residual interstitial gases; and releasing the dividing device, whereupon the liquid component rapidly migrates into the second compartment and thoroughly infuses into the orthopedic graft material component so as to form a hydrated orthopedic graft material.

52. The invention according to claim 51, further comprising removing the hydrated orthopedic graft material from the container.

53. The invention according to claim 52, further comprising fastening the hydrated orthopedic graft material onto the surface of bone tissue.

54. A container for hydrating orthopedic graft material, comprising:
- a chamber containing the orthopedic graft material under at least a partial vacuum;
- a port device capable of allowing the introduction of a liquid into said chamber; and
- a vacuum reservoir capable of drawing the liquid received through said port device into said chamber and infusing said orthopedic graft material with the liquid.

55. The container for hydrating orthopedic graft material according to claim 54, further comprising a graft material selected from the group consisting of allograft material, xenograft material, synthetic material, and combinations thereof.

56. The container for hydrating orthopedic graft material according to claim 54 wherein said port is configured to receive a syringe.

57. The container for hydrating orthopedic graft material according to claim 56 wherein said port is self-sealing.

58. The container for hydrating orthopedic graft material according to claim 54 wherein the liquid is a water based solution.

59. The container for hydrating orthopedic graft material according to claim 58 wherein a solute of said water based solution includes a salt.

60. The container for hydrating orthopedic graft material according to claim 54 wherein the liquid further comprises a biologically active material.

61. The container for hydrating orthopedic graft material according to claim 60, wherein said biologically active material is an antibiotic.

62. The container for hydrating orthopedic graft material according to claim 60, wherein said biologically active material is a platelet concentrate.

63. The container for hydrating orthopedic graft material according to claim 54, further comprising a second chamber capable of receiving the liquid.

64. The container for hydrating orthopedic graft material according to claim 63, further comprising a dividing device for dividing said container between said chamber containing the orthopedic graft material and said second chamber containing the liquid.

65. The container for hydrating orthopedic graft material according to claim 54 wherein said chamber has a first and a second end, said port disposed on said first end, said vacuum chamber disposed on said second end, and wherein said vacuum chamber is configured to draw the liquid from said first end toward said second end through said orthopedic graft material.

* * * * *